United States Patent
Morikawa et al.

(10) Patent No.: US 7,536,270 B2
(45) Date of Patent: *May 19, 2009

(54) SERVICE PROVIDING SYSTEM, DISAPPOINTMENT JUDGING SYSTEM, AND DISAPPOINTMENT JUDGING METHOD

(75) Inventors: Koji Morikawa, Kyoto (JP); Shouichi Araki, Osaka (JP); Shinobu Adachi, Osaka (JP)

(73) Assignee: Panasonic Corporation, Osaka (JP)

( * ) Notice: Subject to any disclaimer, the term of this patent is extended or adjusted under 35 U.S.C. 154(b) by 470 days.

This patent is subject to a terminal disclaimer.

(21) Appl. No.: 11/319,082

(22) Filed: Dec. 27, 2005

(65) Prior Publication Data

US 2006/0101079 A1 May 11, 2006

Related U.S. Application Data

(63) Continuation of application No. PCT/JP2004/009303, filed on Jun. 24, 2004.

(30) Foreign Application Priority Data

Jun. 27, 2003 (JP) ............................. 2003-184162

(51) Int. Cl.
*G01D 1/00* (2006.01)
*G06F 15/00* (2006.01)

(52) U.S. Cl. .................. 702/127; 434/322; 702/82; 707/104.1; 711/162

(58) Field of Classification Search ............ 702/82, 702/127, 186–190; 707/3, 7, 104.1; 700/90; 709/203, 227; 713/193; 715/716; 711/162; 434/322

See application file for complete search history.

(56) References Cited

U.S. PATENT DOCUMENTS

| 4,926,969 | A | 5/1990 | Wright et al. |
| 6,341,960 | B1 * | 1/2002 | Frasson et al. .............. 434/322 |
| 7,007,144 | B2 * | 2/2006 | Nakanishi et al. ........... 711/162 |
| 2008/0097719 | A1 * | 4/2008 | Adachi et al. ............... 702/127 |

FOREIGN PATENT DOCUMENTS

| JP | 05-015599 | 1/1993 |
| JP | 2000-235588 | 8/2000 |
| JP | 2002-281186 | 9/2002 |

OTHER PUBLICATIONS

JP 2002-281186 A, Sep. 27, 2002, Nakamura, English translation.*

(Continued)

*Primary Examiner*—John H Le
(74) *Attorney, Agent, or Firm*—Harness, Dickey & Pierce, P.L.C.

(57) ABSTRACT

A response content determination section determines a response content in response to a request from a user which is received by an input section, and an output section outputs the response content. A biological signal detection section measures a biological signal of the user from an output timing of the output section as a starting point, and a disappointment judgment section judges, based on the biological signal, whether or not the response content matches the request of the user.

8 Claims, 11 Drawing Sheets

OTHER PUBLICATIONS

Kaga et al.; "Manual of Event-related Potentials (ERP)—Centering on P300-"; Shinohara Shuppan Shinsha; 1995; p. 197; and a partial English translation thereof.

Fujisawa et al.; "Neo Physiological Psychology"; Kitaohji Shobo; 1998; p. 108; and a partial English translation thereof.

HIroshi Nittono; "Measurement of Event-related Potentials by Mouse Clicking Paradigm"; Memoir of the Japanese Psychological Association; 67th Annual Convention; Sep. 14, 2003; p. 671; and a partial English translation thereof.

M. Isabel Núñez-Peña et al.; "P600 related to rule violation in an arithmetic task"; Sep. 30, 2003; pp. 130-141.

* cited by examiner

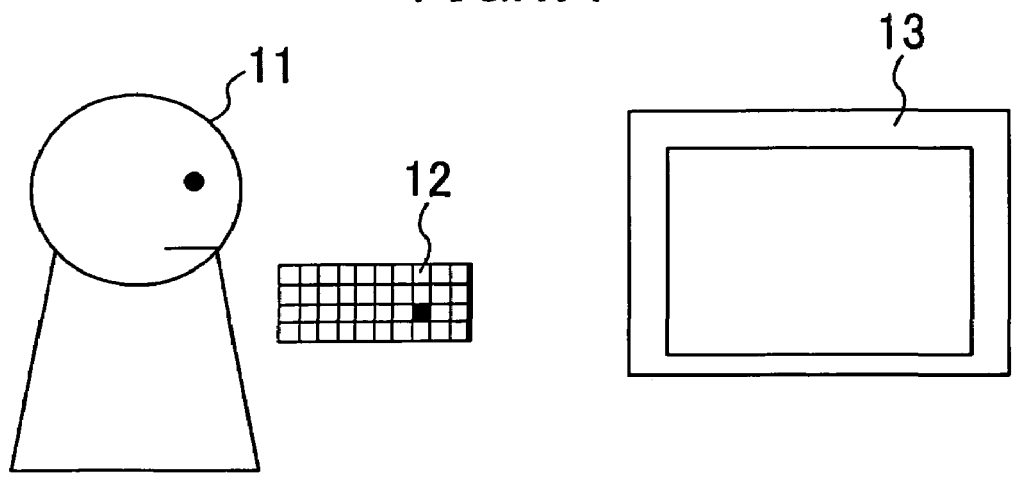
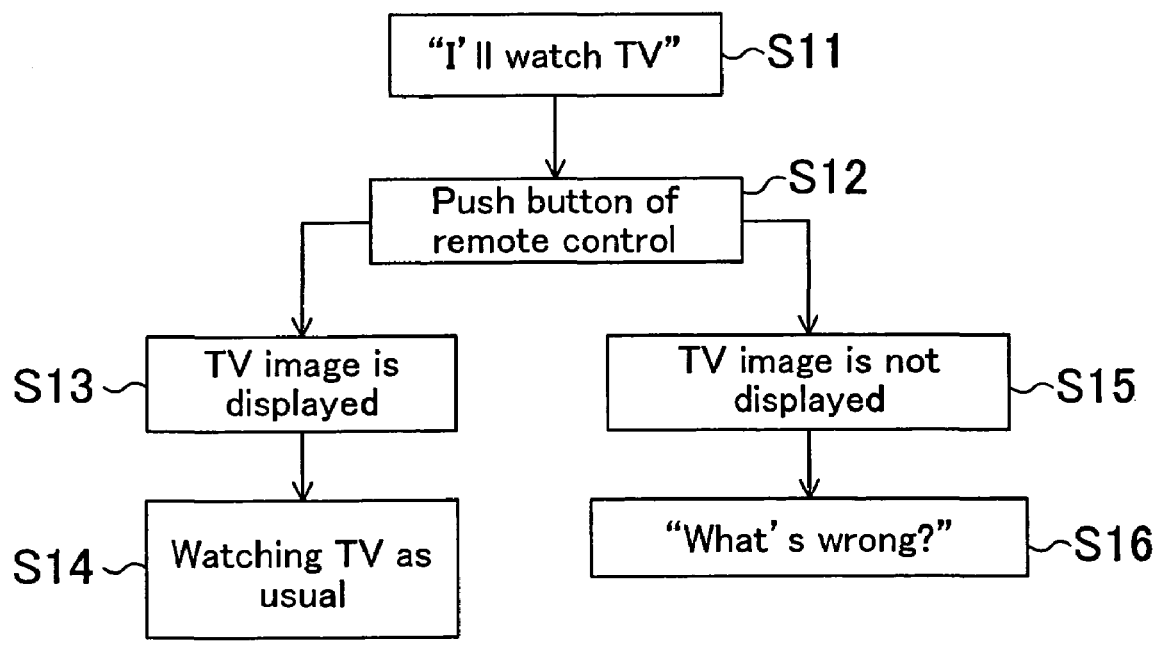

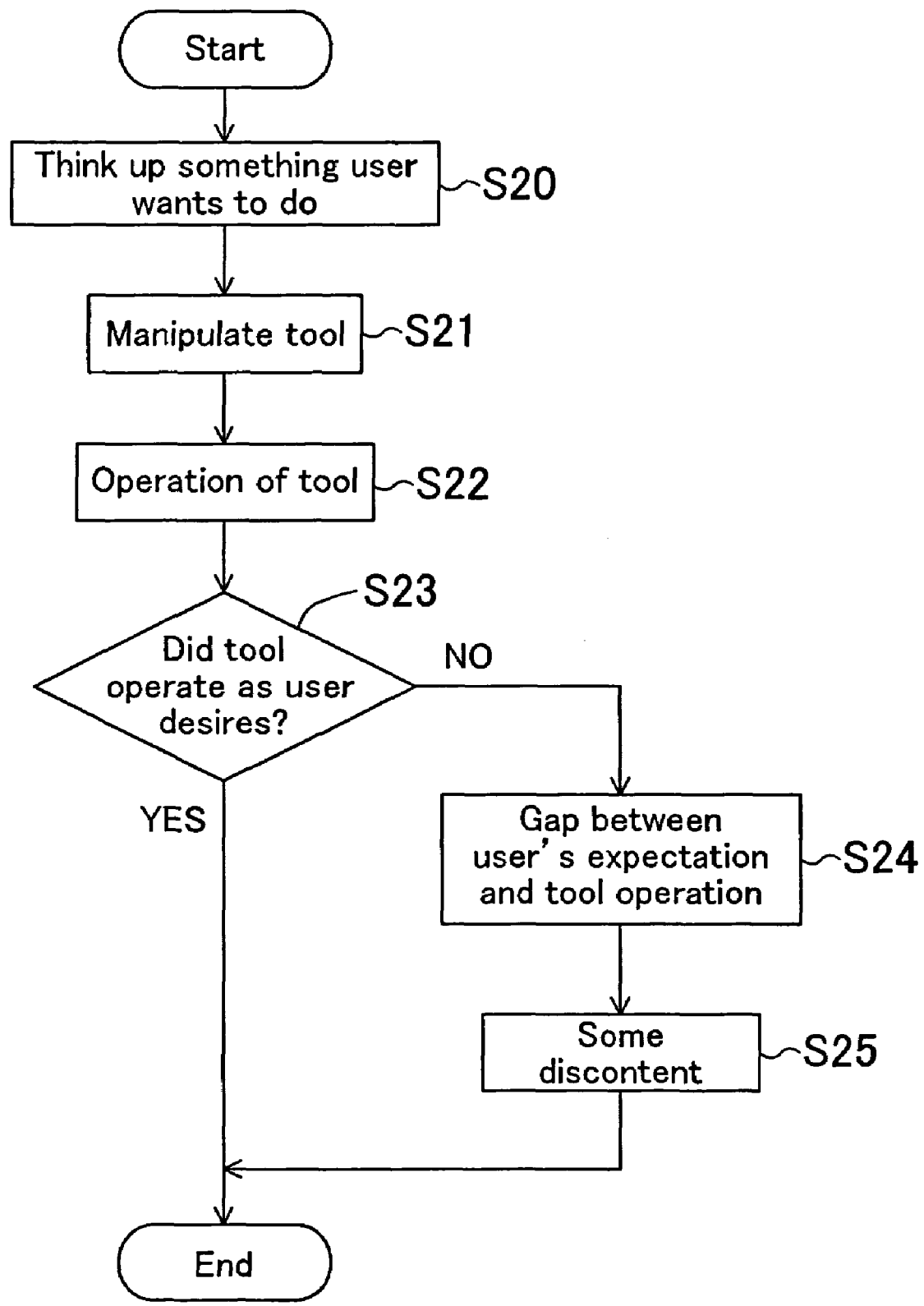

——— Disappointment ——— Normal course

FIG.9

|  | Number of targets | Correct judgment | Identification rate (%) |
|---|---|---|---|
| Subject A | 23 | 18 | 78 |
| Subject B | 17 | 14 | 82 |
| Subject C | 18 | 16 | 89 |
| Subject D | 17 | 13 | 76 |
| Total | 75 | 61 | 81 |

SERVICE PROVIDING SYSTEM, DISAPPOINTMENT JUDGING SYSTEM, AND DISAPPOINTMENT JUDGING METHOD

CROSS REFERENCE TO RELATED APPLICATIONS

This is a continuation of Application PCT/JP2004/009303 filed on Jun. 24, 2004. This Non-provisional application claims priority under 35 U.S.C. § 119(a) on Patent Application No. 2003-184102 filed in Japan on Jun. 27, 2003, the entire contents of which are hereby incorporated by reference.

BACKGROUND ART

The present invention relates to a system for providing some service to a user, such as a home use robot, an information terminal, or the like, and particularly relates to a technology for enabling provision of further appropriate service to user's state.

Recently, appliances are demanded which are capable of providing complicated information or service to a user, such as home use robots, information terminals, and the like and the reduction to practical use thereof are being promoted. Information and service which can be provided through such appliances expand over a wide range and a function capable of performing operation according to user's preference is demanded. Under the circumstances, how suitable operation for user's state can be performed is one of important factors for determining appliance's performance.

Various techniques have been proposed as conventional techniques for detecting user's state. For example, it can be said that input tools such as buttons, key boards, mouses are means for notifying user's request or the like to an appliance. Further, if user's mental state or intention could be detected in addition to the user's request, the appliance could exhibit further advanced adaptability. Particularly, it is desirable to detect a state in which a user feels some discontent. For example, when a user would feel that an appliance does not operate as the user desires, some improved counter-response could be offered if the appliance could detect the user's discontent but the response could not be changed without detection thereof.

Referring to detection of user's discontent, Patent Document 1 discloses a technique that: a user might express discontent through an action of banging an appliance when the appliance performs operation that the user does not desire, and the action of banging or vibration of the appliance is detected to change information that the appliance is providing.

Further, a method of detecting user's state through a biological signal may be considered. For example, Patent Document 2 discloses that measurement and processing of a physiological reaction in electrocardiogram, electroencephalogram, sphygmogram, or the like can attain judgment of an awaking level, an attention level, sleepiness, tiredness, mental burden, physical comfort, or the like.

On the other hand, in cognitive psychology and clinical medical science, study using physiological indexes such as an electroencephalogram (EEG) has progressed. According to Non-patent Document 1, for example, diagnoses of dementia, melancholia, schizophrenia, higher order cognition disorder, and the like and effect judgments of various medicine and rehabilitation are carried out using electroencephalographs.

(Patent Document 1) Japanese Patent Application Laid Open Publication No. 2002-281186A (Patent Document 2) Japanese Patent Application Laid Open Publication No. 5-15599A (Non-patent Document 1) "Manual of Event-Related Potentials (ERP)—Centering on P300-," by Kaga et al., published by Shinohara Shuppan Shinsha, 1995

(Non-patent Document 2) "Neo Physiological Psychology," by Fujisawa et al., published by Kitaohji Shobo, 1998

Problems That the Invention is to Solve

Targets to be detected in the aforementioned conventional techniques were user's active action (appliance's banging by a user, for example), user's tiredness, user's discontents, and the like. However, appliance's banging by a user, user's discontents at an appliance, and the like result from accumulation of inappropriate responsive operation of the appliance such as operation of the appliance different from user's request, disappointing operation, and the like.

Accordingly, if user's mental states or intentions towards individual responsive operations could be detected rather than detection of discontent that has been already caused, the adaptability of the appliance to users could be improved further. For example, if that a user thinks "Why?" to a certain responsive operation would be detected, the responsive operation could be modified before the user feels discontent caused by repetition of such responsive operation. This prevents users from feeling discontent.

The present invention has been made in view of the above problems, and has its objective of enabling provision of service more appropriate to users' states by grasping users' mental states and intentions towards responsive operations.

SUMMARY OF THE INVENTION

The present invention provides a service providing system including: an input section that receives user's request; a response content determination section that determines a response content in response to the user's request received by the input section; an output section that outputs the response content determined by the response content determination section; a biological signal detection section that measures a user's biological signal from a timing, as a starting point, when the output section outputs the response content; and a disappointment judgment section that judges, base on the biological signal measured by the biological signal detection section, whether or not the response content matches the user's request.

According to the present invention, the service providing system measures, upon output of a response content determined in response to user's request, user's biological signal from a timing of the output as a starting point. Then, whether or not the output response content matches the user's request is judged based on the measured biological signal. Accordingly, information as to whether or not the response matches user's expectation can be obtained from the user's biological signal. This enables modification of the response content, learning of the relationships between the user's request and the response content, and the like, thereby providing more appropriate service to the user.

In the service providing system according to the present invention, it is preferable that the biological signal detection section includes an electroencephalograph and measures an event-related potential in an electroencephalogram as the biological signal.

BRIEF DESCRIPTION OF THE DRAWINGS

FIG. 1(a) shows a state in which a user manipulates an appliance and FIG. 1(b) is a flowchart showing user's thought and action in FIG. 1(a).

FIG. 2 is a flowchart in which FIG. 1(b) is generalized.

FIG. 9 is a table showing results of detection of the disappointment signal.

DESCRIPTION OF THE PREFERRED EMBODIMENTS

Figure 3:
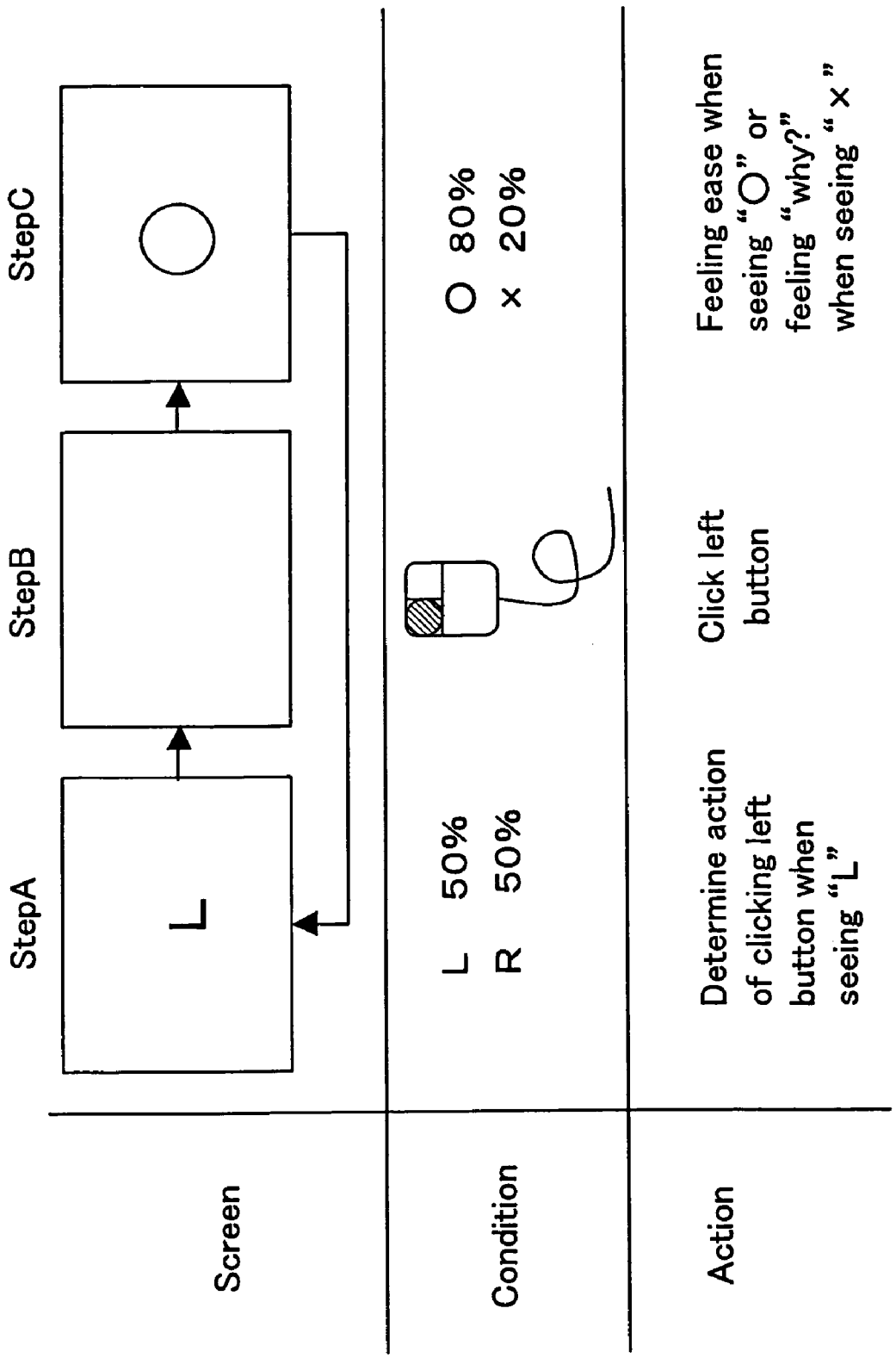
FIG. 3 is an illustration showing a scheme in sequence of an experiment that the inventors carried out.

A first aspect of the present invention provides a service providing system including: an input section that receives user's request; a response content determination section that determines a response content in response to the user's request received by the input section; an output section that outputs the response content determined by the response content determination section; a biological signal detection section that measures user's biological signal from a timing, as a starting point, when the output section outputs the response content; and a disappointment judgment section that judges, base on the biological signal measured by the biological signal detection section, whether or not the response content matches the user's request.

A second aspect of the present invention provides the service providing system of the first aspect, wherein the biological signal detection section includes an electroencephalograph and measures an event-related potential in an electroencephalogram as the biological signal.

A third aspect of the present invention provides the service providing system of the second aspect, wherein the disappointment judgment section performs judgment using a part of the biological signal around approximately 600 ms after the starting point.

A fourth aspect of the present invention provides the service providing system of the second aspect, wherein the disappointment judgment section performs judgment using a part of the biological signal around time obtained by adding or subtracting time according to complication of the response content or user's characteristic to or from approximately 600 ms after the starting point.

A fifth aspect of the present invention provides the service providing system of the second aspect, wherein the disappointment judgment section performs judgment using a signal template for disappointment.

A sixth aspect of the present invention provides the service providing system of the first aspect, further including: a learning section that learns a relationship between the user's request and the response content with the use of a judgment result by the disappointment judgment section.

A seventh aspect of the present invention provides the service providing system of the first aspect, wherein help indication is provided as service.

An eighth aspect of the present invention provides the service providing system of the first aspect, wherein service is provided as an agent.

A ninth aspect of the present invention provides the service providing system of the first aspect, wherein service is provided through natural conversation.

The present invention is provided for detecting user's feeling of "disappointment" utilizing variation in user's biological signal which is induced by responsive operation of a system. Herein, an event-related potential in an electroencephalogram is used as an example of the biological signal.

(Event-Related Potential)

The event-related potential (ERP) means signal variation induced in response to some stimulation in an electroencephalogram (see Non-patent Document 1). This signal variation is considered to relate to an error control mechanism of a processing system within a brain. In generally-called oddball task, for example, the signal variation is not detected when a human being listens to a sound series as he/she predicts but is detected at the instant when a sound series contrary to his/her prediction appears. The event-related potential is considered to relate also to higher order activity in human cognition and have been employed in cognition study and clinical diagnosis and treatment of diseases.

Figure 11:
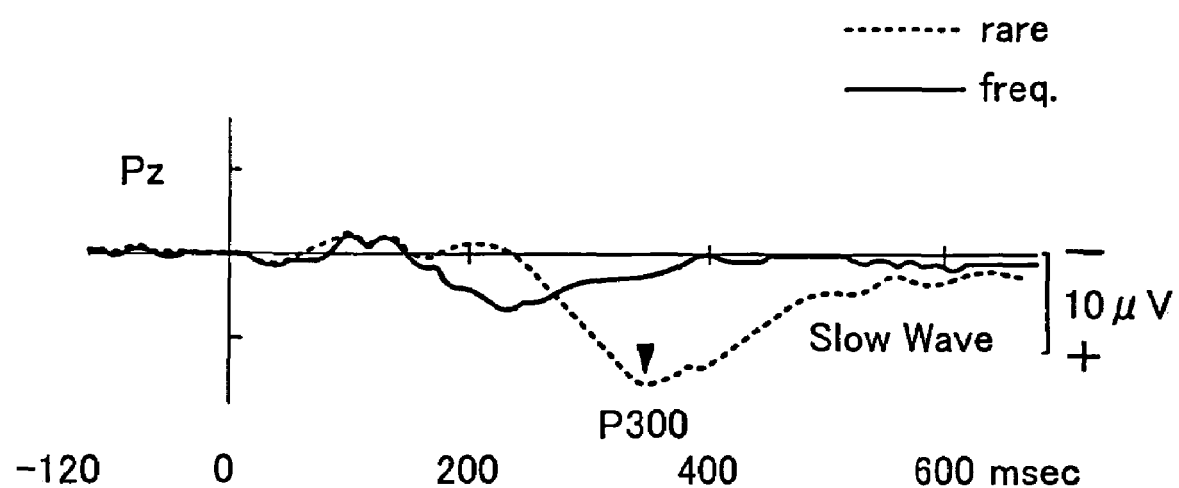
FIG. 11 is a graph showing an example of an event-related potential.

FIG. 11 is a graph showing an example of the event-related potential (see page 12 of Non-patent Document 1). FIG. 11 shows variation in an electroencephalogram at a reaction to oddball task, wherein the solid line indicates a reaction to stimulation (frequent stimulation) often provided in the task and the broken line indicates a reaction to stimulation (rare stimulation) provided sometimes in the task. The axis of abscissas indicates time and the axis of ordinates indicates voltage. As can be understood from FIG. 11, the potential largely changes in response to the rare stimulation after several hundreds milliseconds from the stimulation. This might be because: the rare stimulation is provided when the frequent stimulation is predicted, so that a prediction error that "this is different from usual one" occurs. In the broken line in FIG. 11, a large amplitude is observed at around 300 ms after provision of the stimulation and this signal is usually called P300.

P300 can be used for measurement of an ability as to whether or not an attention can be directed intentionally towards sound or the like. Accordingly, diagnoses of dementia, melancholia, schizophrenia, higher order cognition disorder, and the like and effect judgments of various medicine or rehabilitation are carried out using P300.

Challenge of applying the event-related potential like P300 in an electroencephalogram to cognition study for clarifying brain functions and human diagnoses and treatments (mental disorder, higher order cognition disorder, and dementia) has been promoted.

(Conception of the Present Invention)

The present inventors hit on an idea that a biological signal like the event-related potential is applied to an interface of an appliance. In detail, in a system for providing service such as information or the like to users, an output thereof might induce some variation in users' physiological state. For example, when a response content that a system provides is different from user's expectation, the user might be disappointed and think "Why?"

If such user's "disappointment" could be detected from a biological signal, further appropriate service could be provided to the user by, for example, changing the response content or learning not to induce the "disappointment." This prevents the user from feeling discontent at the appliance and in turn from non-use of the appliance.

FIG. 1(a) is a schematic view showing a state in which a user manipulates an appliance. The user 11 is trying to manipulate the appliance 13 such as a TV set with the use of a manipulation tool 12 such as a remote control, a keyboard, or the like. In the state shown in FIG. 1(a), the flow as shown in FIG. 1(b) can be considered as to mind and behavior of the user 11. When the user 11 thinks up "I'll watch TV" (S11), the user 11 takes up the remote control 12 in front of him/her and pushes a power switch (S12). When the user appropriately pushes the switch and no problem is involved in the TV set 13, the TV set 13 turns ON to display an image (S13). The user 11 watches the TV 13 as it is as usual (S14). This is the normal course of steps. In contrast, if the TV set displays no image (S15) even though the power switch of the remote control 12 is pushed, the user 11 would think "What's wrong with it?" (S16).

FIG. 2 is a flow in which FIG. 1(b) is generalized and expressed. The user thinks up something he/she wants to do first (S20) and manipulates a tool (S21), and then, the tool operates in response to the user's manipulation (S22). When the user observes the tool's operation, the user feels whether or not the tool operated as he/she desires (S23). If the tool would operate differently from his/her desire (NO in S23), a gap is generated between the user's expectation and the tool's operation (S24). This might make the user to feel discontent (S25). However, the discontent that the user feels at that time may be a feeling of negligible wrongness to a degree that it is uncertain whether or not the user recognizes the "discontent".

Under the circumstances, if information as to whether or not the tool operates as the user desires (the branch at S23) could be obtained as a signal, this information could be an important information source for usability of the appliance. Whether or not such an important information source can be obtained by measuring a biological signal such as the event-related potential is the source of idea of the present invention. Wherein, in the description of the present application, a signal detected when a tool operates differently from user's desire is called a "disappointment signal."

(Experiment for Obtaining Disappointment Signal)

An experiment for obtaining the disappointment signal, which the present inventors carried out, will be described below.

FIG. 3 is an illustration showing a scheme in sequence of the experiment. This experiment is composed of sequential steps of: providing an instruction to a subject (Step A); in response to the instruction, allowing the subject to think about necessary action and to manipulate a tool (Step B); and presenting tool's operation to the subject as a result of the subject's manipulation (Step C).

First, an experiment executer explains to a subject "When a letter 'L' or 'R' is indicated in a screen, please click the left button of a mouse for the letter 'L' or click the right button thereof for the letter 'R'." Then, "L" or "R" is selected at random at a probability of 50% and is displayed on the screen (Step A). The subject looks at the displayed letter and clicks the right or left button in accordance with the directed rule (Step B). In response to the subject's manipulation, whether or not the correct button was clicked is displayed as "○" symbol (indicating a correct answer) or "x" symbol (indicating an incorrect answer) on the screen (Step C).

Wherein, even when a correct button is clicked (clicking might be almost 100% correctly done), "x" is displayed at a probability of 20% in this experiment. When "x" is displayed, the subject, who is expecting that "○" will be displayed because of correct clicking, might think "Why?" Namely, the subject falls in a "disappointment" state in which the tool operates differently from his/her expectation. This experiment is aimed at confirming whether or not this "disappointment" state can be detected from the event-related potential in an electroencephalogram.

Figure 4:
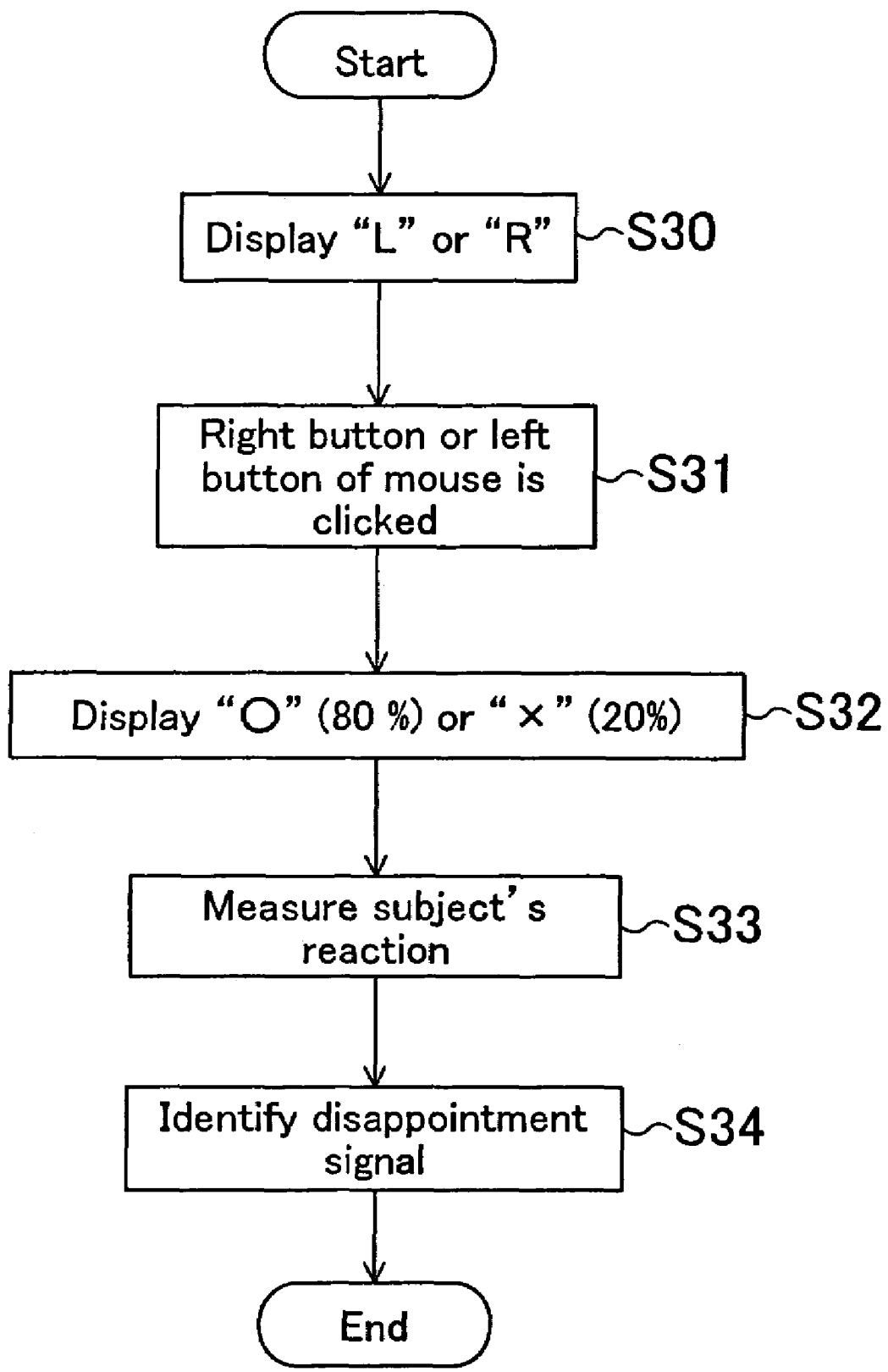
FIG. 4 is a flowchart showing a sequence for one trial of the experiment in FIG. 3.

FIG. 4 is a flowchart showing a sequence for one trial. First, the letter "L" or "R" is selected at a probability of 50% and is displayed on the screen (S30), the subject looks at the screen, selects which button is to be clicked, and manipulates the mouse (S31). In response to the subject's manipulation, "○" or "x" is displayed on the basis of whether or not the mouse is operated correctly. Wherein, "x" is displayed at a probability of 20% even when "○" should be displayed (S32). The event-related potential in the electroencephalogram of the subject is measured from the timing when "○" or "x" is displayed as a starting point (S33), and the thus measured event-related potential is processed to identify the disappointment signal (S34).

In the experiment, to a plurality of subjects, a trial in which "○" is displayed every time was carried out 30 times as practice first, and then, the trial through the sequence shown in FIG. 4 was carried out 100 times.

Figure 5:
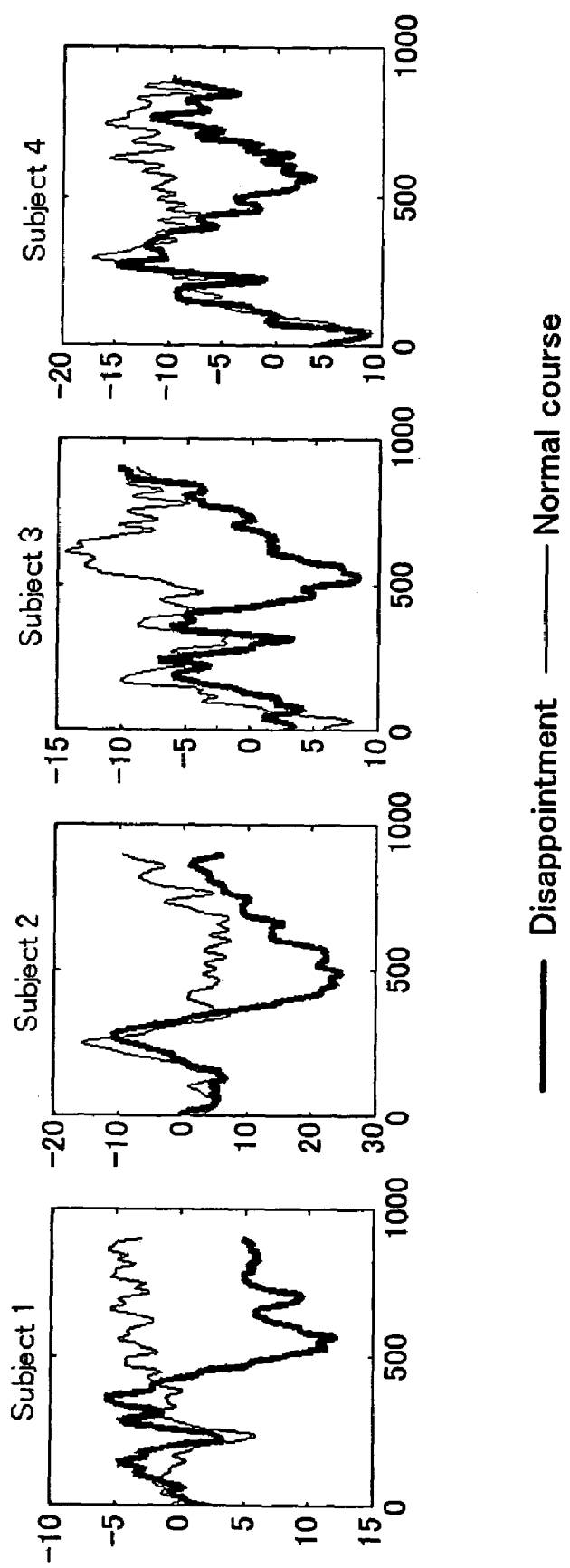
FIG. 5 includes graphs indicating experiment data of four subjects.

FIG. 5 includes graphs showing experiment data of four subjects (Subjects 1 to 4) out of the experiment results. Each graph in FIG. 5 was obtained by integrating potential waveforms measured by an electroencephalograph, wherein each axis of abscissas indicates elapsed time from stimulation provision (the time when "○" or "x" is displayed, unit: ms) and each axis of ordinates indicates potential (unit: μV). Each bold line indicates "disappointment," that is, a waveform obtained when "x" was indicated in response to correct clicking and each fine line indicates a normal course, that is, a waveform obtained when "○" was indicated in response to correct clicking. Wherein, four electrodes 1) Pz, 2) and 3) A1 and A2, and 4) body earth (Z) were attached to a median vertex, respective ears, and a root of nose, respectively in accordance with the international 10-20 system. The sampling frequency was set to be 1000 Hz.

It is understood from each graph in FIG. 5 that at disappointment, an event-related potential having a characteristic different from that of a potential at the normal course appeared around approximately 600 ms after the stimulation provision. Namely, it is expected that measurement of the event-related potential leads to detection of user's disappointment.

Wherein, in the event-related potential measured in this experiment, time of the reaction in response to the stimulation provision was late to some extent in comparison with the aforementioned P300. The reason therefor might be as follows though it is uncertain.

The experiments conventionally carried out in relation to event-related potentials (Non-patent Documents 1, 2, and the like) were experiments through measurement of passive reactions of judgment on difference in musical interval or in image. In contrast, in the experiment that the present inventors carried out, an action was selected with a certain expectation and whether or not operation was performed as expected was judged. The feature that the step of selecting an action by a user is included is the significant difference from the conventional ones. The judgment as to whether or not the operation is performed as a subject expects is cognitive judgment compared with the mere judgment of difference in sound or in image. For this reason, the reaction time after the stimulation provision might be slightly later than that in the measurements in the conventional experiments, resulting in a peak around 600 ms the after stimulation provision. It is noted that the timing when a peak appears is different from subject to subject, as can be understood from FIG. 5. Further, they are different from trial to trial.

As clarified through the experiment, the event-related potential measured by the electroencephalograph offers apparent difference between the case where the tool operates as a user expects and the case where it operates differently from user's expectation. Accordingly, the event-related potential can be used as the "disappointment signal" in the interface of an appliance.

Figure 6:
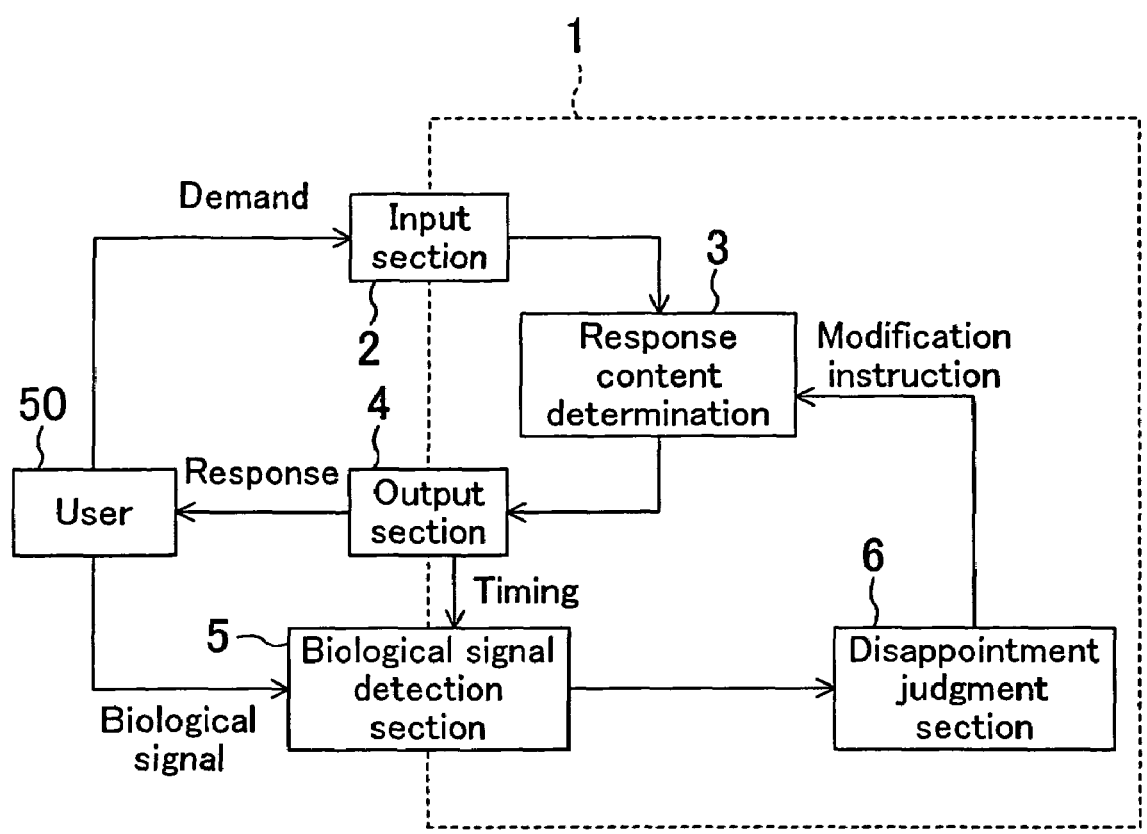
FIG. 6 is a block diagram showing a constitution of a service providing system according to one embodiment of the present invention.

FIG. 6 is a block diagram showing a constitution of a service providing system according to one embodiment of the present invention. Specifically, home use robots, information terminals, home use appliances which are required to respond according to user's request correspond to this service providing system.

In FIG. 6, the service providing system 1 includes: an input section 2 that receives a request from a user 50; a response content determination section 3 that determines a response content in response to the request received by the input section 2; an output section 4 that outputs the response content determined by the response content determination section 3; a biological signal detection section 5 that measures a biological signal of the user 50 from a timing, as a starting point, when the output section 4 outputs the response content; and a disappointment judgment section that judges whether or not the response content matches the request of the user 50 based on the biological signal measured by the biological signal detection section 5.

The user 50 can exchange information and the like with the service providing system 1 through the input section 2 and the output section 4. For example, the input section 2 is composed of a mouse, a keyboard, an audio input apparatus, or the like and the output section 4 is composed of a screen for displaying a text, an image, or the like, an audio output apparatus for performing a response in the form of synthetic sound, an actuator, or the like. Further, the user fits in advance an electroencephalograph that composes the biological signal detection section 5.

Figure 7:
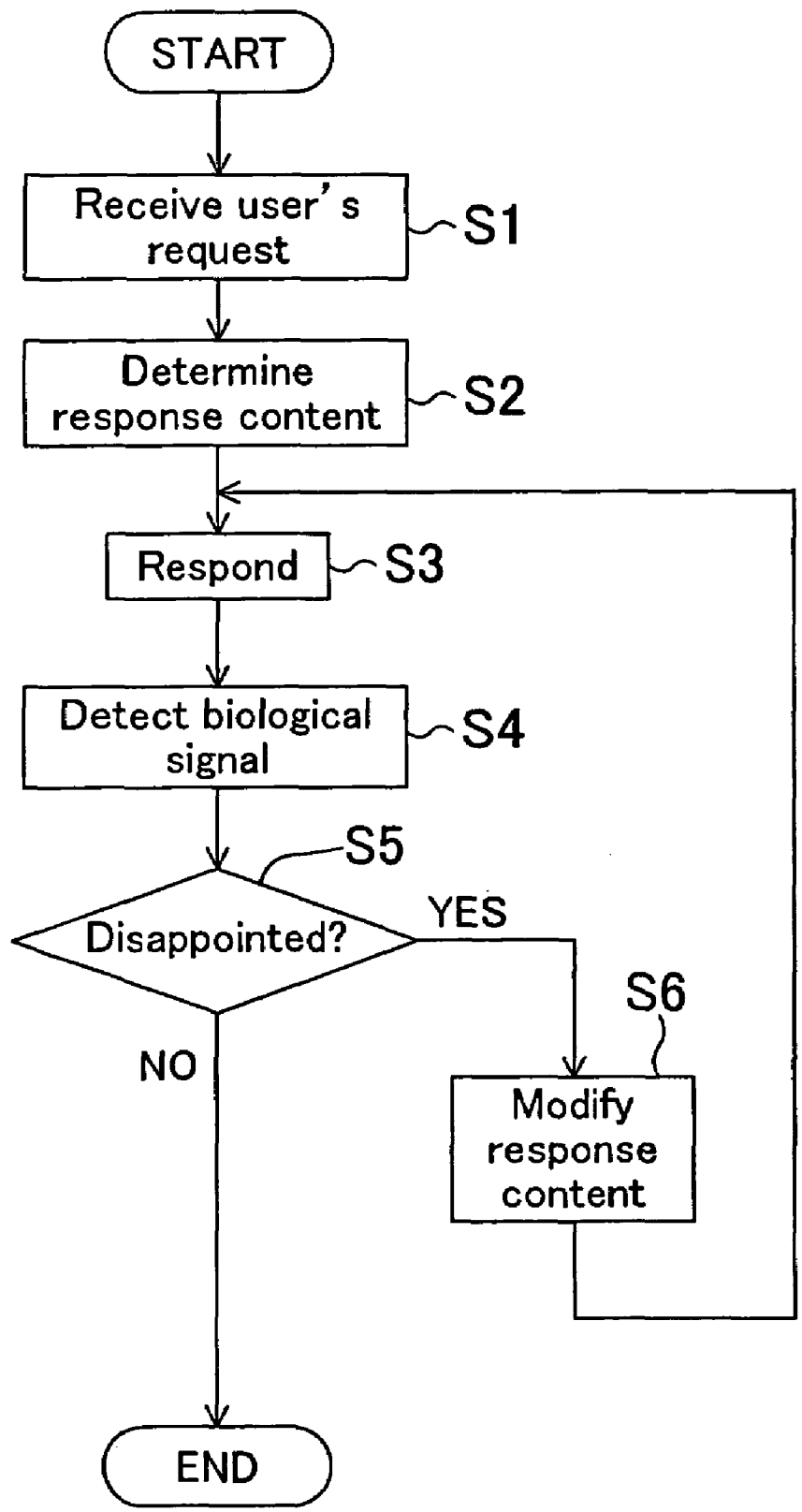
FIG. 7 is a flowchart showing operation of the service providing system in FIG. 6.

Operation of the service providing system in FIG. 6 will be described below with reference to the flowchart of FIG. 7.

First, the input section 2 receives a request from the user 50 (S1). The user 50 specifies, for example, a genre of information, a desired service content, or the like in information provision through the input section 2.

When the input section 2 receives the request from the user 50, the response content determination section 3 determines a response content in response to the request (S2). For example, a content of information to be provided is determined. When the response content determination section 3 determines the response content, the output section 4 outputs the response content (S3). For example, the content of information to be provided is displayed on the screen.

When the output section 4 outputs the response content, the biological signal detection section 5 measures a biological signal of the user 50 from that timing as a starting point (S4). At that time, the user 50 might indicate a different biological reaction according to whether or not the output response content was one as his/or expected. Herein, an event-related potential in an electroencephalogram is measured by the electroencephalograph that the user 50 fits in advance.

Then, the disappointment judgment section 6 judges, from the biological signal measured by the biological signal detection section 5, whether or not a "disappointment signal" is detected, namely, whether or not the output response content matches the user's request (S5).

When the "disappointment signal" is detected (YES in S5), the output response content might not match the user's expectation, and accordingly, the disappointment judgment section 6 outputs a modification instruction to the response content determination section 3. The response content determination section 3 modifies the response content (S6), and then, the modified response content is output again through the output section 4 (S3). For example, in the case of an information provider, it may ask "Sorry. Wouldn't you prefer it?" or provide another piece of information with a comment "Would you like this one?" or the like.

The case where the system operates differently from the user's expectation may occur in the following cases:

(1) A tool operating model that a user has is wrong.

For example, when a user desires to turn an appliance ON, the user looks around the appliance and/or a remote control to look for a power switch and contemplates what kind of manipulation he/she should take for turning the appliance ON. Then, he/she selects and takes an action for appliance manipulation. If the manipulation that the user has taken took would be wrong, the appliance does not operate as the user expects naturally, and accordingly, a "disappointment signal" is detected.

The user falls in a state in which the appliance does not operate in actual fact though the user expects that "this manipulation might turn the appliance ON." This means that the tool operating model that the user has does not accord with the actual operating model of the appliance.

For dealing with this case, two sorts of operations can be proposed: (A) to modify the user's tool operating model; and (B) to modify the tool operating model of the appliance. In the above example, solutions shall be notification of the position of the power switch to the user for the case (A) and to turn the appliance ON even by the user's wrong manipulation for the case (B). Of course, these are based on the assumption that the operation that the user expects is known. Wherein, even in the case where operation that the user expects is unknown, whether or not the appliance operates as the user expects serves, if it could be detected, as important information for controlling the appliance.

(2) A user's preference model is wrong.

In service for providing information suitable for a user, the system is required to grasp what the user prefers, that is, user's preference model. As long as user's preference that a system has is different from actual user's preference, the user feels that "the system does not provide information as he/she expects," and therefore, the "disappointment signal" is detected.

For dealing with this case, there may be proposed: to modify the user's preference model and perform information provision again; to continue recommending the provided information for it might be valuable to the user; and the like. Only if whether or not the information provision matches the user's expectation could be detected, this would serve as useful information for learning user's preference model.

(Detection of Disappointment Signal)

A specific example of a disappointment signal detection method will be described with reference to the flowchart of FIG. 8. In this method, a standard waveform (a target template) to which a signal at disappointment is added and another standard waveform (referred to as a control template) to which a signal in a non-disappointed normal state is added are generated in advance and these templates are utilized for detection of the "disappointment signal."

Figure 8:
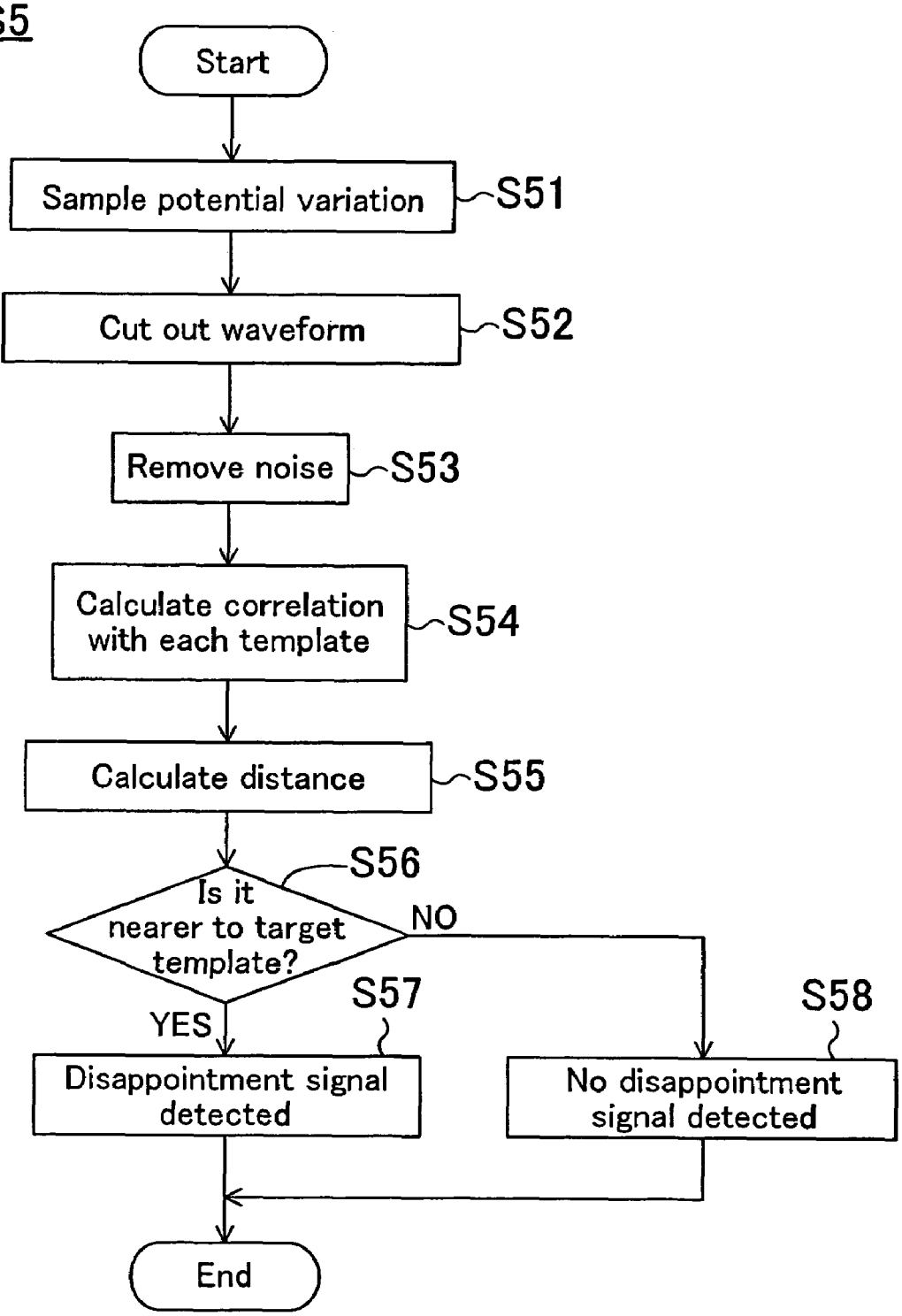
FIG. 8 is a flowchart showing an example of a specific method for detecting a disappointment signal.

As shown in FIG. 8, first, potential variation in an electroencephalogram is sampled (S51) from a timing, as a starting point, when the output section 4 outputs a response content (at response presentation). The sampling frequency may be 200 Hz, 500 Hz, 1000 Hz, or the like, for example. Then, a waveform in a range relating to detection of the "disappointment signal" is cut out from the thus obtained potential variation in the electroencephalogram (S52). From the results of the above described experiment, it is known that the "disappointment signal" is detected at a part around 600 ms after stimulation provision. Further, in a comparatively earlier range after response presentation, a waveform appearing in response to aural stimulation or visual stimulation is considered to have no relationship with human's expectation, and therefore, the part corresponding thereto is preferable to remove. As such, the range between 200 ms and 800 ms after the response presentation is cut out.

Of course, the cut out range is not limited thereto and may be set in a range between 500 ms and 700 ms, between 300 ms and 900 ms, or the like. Alternatively, a range within approximately 1 second after the response presentation may be cut out with no lower limit set.

Next, noise is removed from the cut out waveform (S53). Herein, high-frequency components mixed with the signal is cut, the signal is allowed to pass through a low-pass filter of, for example, 40 Hz, a waveform with an amplitude over 40 μmV is removed from an object to be identifed for reducing influence of electrooculogram (EOG) by a blink, or the like.

Subsequently, each correlation between the signal from which nose is removed and the signal templates of the target template and the control template is calculated (S54). This correlation calculation calculates how the signal waveform correlates with each template.

Each distance between the signal waveform and the templates is calculated (S55). For example, Mahalanobis distance is employed for the distance calculation. This Mahalanobis distance indicates a distance from a gravity of a group taking account of variance and covariance of data. With the use of Maharanobis distance, judgment is performed as to which template the signal waveform is nearer (S56). It is known that the judgment utilizing Maharanobis distance exhibits higher recognition ability than judgment according to mere magnitude correlation.

When it is judged that the signal waveform is nearer to the target template (YES in S56), it is recognized that the disappointment signal is detected, namely, that the user might be disappointed (S57). On the other hand, when it is judged that the signal waveform is near the control template (S58), it is recognized that the disappointment signal is not detected, namely, that the user thinks that the response as expected is obtained.

Employment of the method using such templates enables detection of the disappointment signal to some extent in an electroencephalogram, of which waveform includes severe variation, and accordingly, of which recognition from a single waveform is considered to be difficult.

FIG. 9 is a table showing results of disappointment signal detection in accordance with the flow of FIG. 8 using the aforementioned experiment data. FIG. 9 indicates the number of targets of each subject (number of data of disappointment) and the number of times of correct judgment. It is understood from FIG. 9 that the state of disappointment can be recognized at an accuracy of approximately 80% even from a single waveform.

It is noted that the signal templates of the target template and the control template are used herein but only the target signal template may be used. For example, Maharanobis distance from the target signal template is calculated and is compared with a predetermined value to judge whether or not the disappointment signal is detected.

It is also noted that another method may be employed rather than the use of a template or in combination with the use of a template. For example, a local maximum or a local minimum may be used, or it is possible that a maximum positive component in a waveform is detected and the amplitude thereof is compared in magnitude with a threshold value. Alternatively, an adaptive correlating filter may be used. It might be possible to provide various additional improvements in the waveform recognition method, and the recognition accuracy might be increased by, for example, combination of a pattern recognition method and a pretreatment method for an electroencephalogram signal.

While, when a presented response content is complicated indication, for example, it may take time for a user to recognize the content. In this case, it is assumed that a peak is observed behind 600 ms. For this case, a disappointment signal may be detected from a signal at a part around a center of time obtained by adding or subtracting a peak time lag to or from 600 ms. This lag time may be obtained in advance by an experiment using a content to be presented for measurement, or the like. Further, factors in determining the lag time might include, for example, user's characteristics such as user's individuality, age, and the like, in addition to complication of a presented response content such as an image, and the like.

Figure 10:
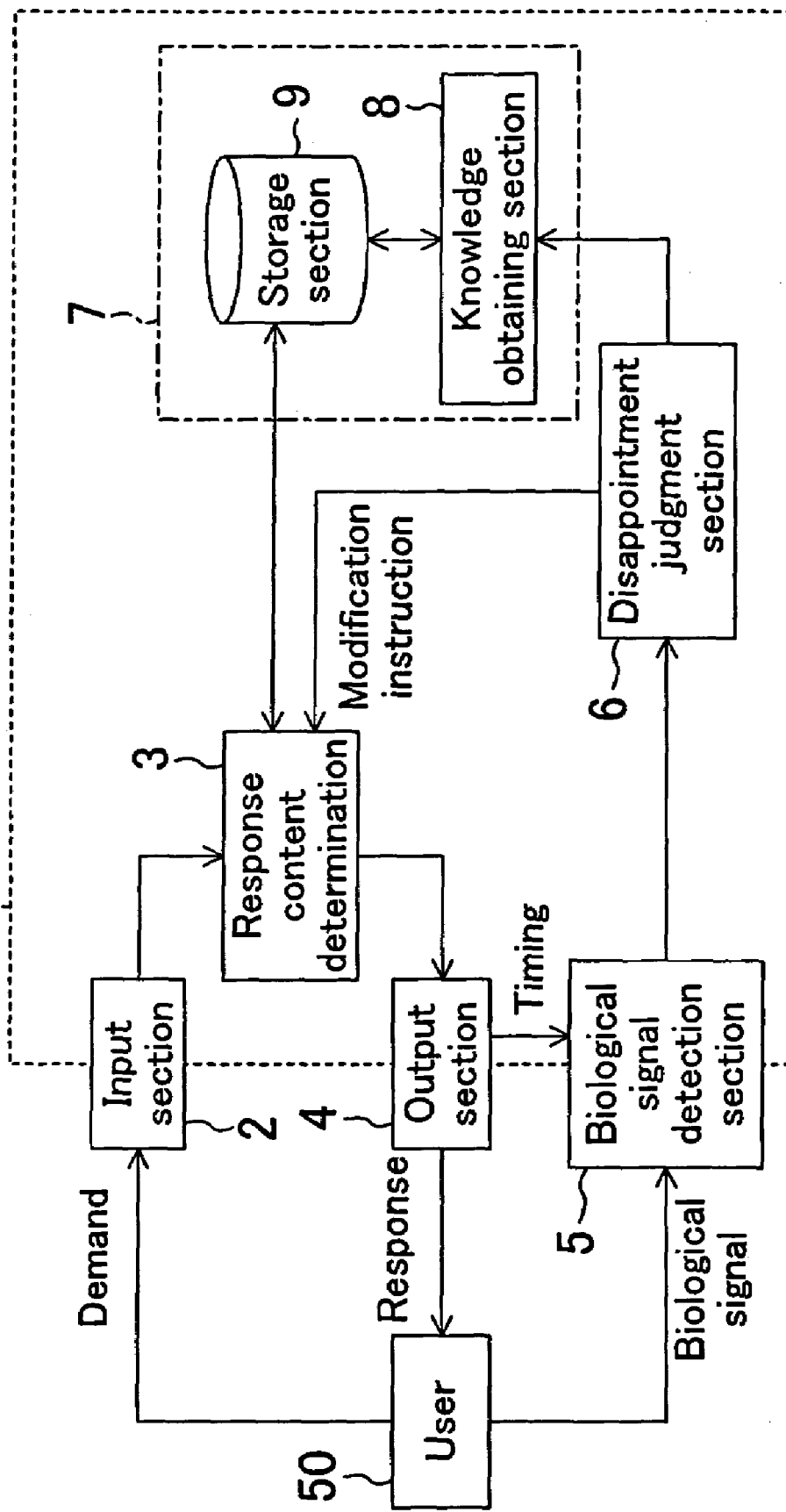
FIG. 10 shows another example of the constitution of the service providing system according to one embodiment of the present invention.

FIG. 10 shows another example of the constitution of the service providing system according to the present embodiment. In FIG. 10, the same reference numerals are assigned to the constitutional elements common to those in FIG. 6. The service providing system 1A in FIG. 10 further includes a learning section 7 that learns a relationship between a request from the user 50 and a response content using a judgment result by the disappointment judgment section 6.

In the learning section 7, a storage section 9 stores rules as to what kind of response should be output from the output section 4 in response to a request from the user 50 which the input section 2 inputs. These rules are expressed by, for example, a rule format such as IF (a signal from a user) and THEN (an action to a user), or the like. Further, a reliability level in the range between 0 and 1 is attached to each rule. The reliability level is a value indicating to what degree the rule is appropriate to a user, and it can be said that the rule is more reliable as the value approximates more to 1.

Upon receipt of a request from the user 50 through the input section 2, the response content determination section 3 extracts from the storage section 9 rules of which antecedents agree with the request and determines as a response content a description content of a consequent of a rule which has the highest reliability level out of the extracted rules, for example.

When the disappointment signal is not detected by the disappointment judgment section 6, a knowledge obtaining section 8 judges that it is highly probable that the system 1A provides an appropriate response and the reliability level of the rule, based on which the response content is determined, is raised so that the same response will be determined in the next time. On the other hand, when the disappointment signal is detected, it is judged that it is highly probable that the response of the system 1A is not appropriate and the reliability level, based on which the response content is determined, is lowered so that another rule will be used in the next time.

As described above, the knowledge obtaining section 8 modifies a rule stored in the storage section 9 using a judgment result by the disappointment judgment section 6, so that updated new rule group is referenced in determining a response content when a similar request is input. This reduces disappointment of the user 50. Further, if the knowledge obtaining section 8 removes or adds a rule according to needs, the storage section 9 can store appropriate knowledge.

(Application Example of the Present Invention)

(1: Help Indication System)

A help indication system is a system for indicating help information appropriate to user's action. If whether or not presented help information matches a request from a user, namely, whether or not it disappoints a user could be judged at presentation of the help information, help indication could be executed more appropriately. Hence, the application of the present invention attains a help indication system offering increased convenience.

For example, suppose that a user selects a mailing function in a mobile phone or a personal computer. In so doing, the user may think to merely and vaguely send an e-mail or to input a mail address first with information necessary for mail sending such as a receiver's mail address, a subject, a body, and the like known. Namely, necessary help information differs even if user's manipulation is the same.

According to the present invention, whether or not the system provides a response as a user expects can be judged, enabling discrimination of the above two cases. For example, guidance on information necessary for mail sending for the former case or a specific manipulation scheme for inputting individual information for the latter case may be provided as help information.

(2: Agent)

An agent means a robot realized in the form of a home use robot, for example, and is a robot which receives user's desire through a language or another interface and provides service such as transport of an object, tool operation, information provision, or the like. In the case where the robot itself does not transport any object nor move, it is realized as an intellectual software agent.

Wherein, user's instructions often accompany vagueness. For example, "Take that," "Recommend an amusing program," and so on. These instructions implicitly indicate an object, which a user clearly desires, and the user requests service in relation thereto.

The robot receives such a vague instruction and provides to a user service that might be the most appropriate according to past learning results. However, service as a user desires would not necessarily be provided every time.

Under the circumstances, according to the present invention, user's reaction to provided service is observed and whether or not the service matches user's expectation is judged. This enables examination of another service upon disappointment and such a fact can be learned immediately as a new rule. As a result, capability of providing service as a user desires in response to user's vague instruction is enhanced further from the next response.

Similarly, the present invention is applicable to services of information recommendation through a TV program or a personal computer.

(3: Natural Conversation)

The present invention is applicable to a constitution employing communication through natural conversation between a user and an appliance. Namely, even in the case of communication or information provision through natural conversation, more smooth communication can be realized when the appliance knows whether or not it operates as a user expects.

In conversation between human beings, they changes the content of a topic that they are taking and the like according to non-language information such as a body gesture, an insignificant motion, variation in facial expression, and the like in addition to language information that they are actually talking. However, a method for identifying non-language information is still in the research-and-development stage, and cannot be said that it is accomplished.

Under the circumstances, whether or not the content of a response to user's talk matches user's expectation is judged according to the present invention. This can restrain a response different from the user's expectation from being output in the next similar situation.

For example, upon detection of disappointment, the content of the conversation may be changed with a comment, "Then, how about this topic?" or the user's intention may be confirmed by presenting "Is this wrong?" Alternatively, that the system recognizes user's disappointment is informed by presenting "Sorry." If the user feeling disappointment could know that the system recognizes it, his/her disappointment may be mitigated to some extent.

In addition, in the present invention, user's reaction can be recognized from a biological signal immediately after a response by an appliance, enabling the appliance to perform immediate counter-response.

According to the present invention, information as to whether or not a system could provide a response as a user expects can be obtained from user's biological signal, enabling provision of service more appropriate to the user. Thus, the present invention is useful for enhancing convenience of a system for providing some service to a user, such as home use robots, information terminals, and the like.

What is claimed is:

1. A service providing system, comprising
   an input section that receives user's request;
   a response content determination section that determines a response content in response to the user's request received by the input section;
   an output section that outputs the response content determined by the response content determination section;
   a biological signal detection section that measures user's event-related potential from a timing, as a starting point, when the output section outputs the response content; and
   a judgment section that judges user's disappointment using a part around approximately 600 ms after the starting point of the event-related potential measured by the biological signal detection section and instructs modification of the response content of the response content determination section with the judgment result referenced.

2. The service providing system of claim 1,
   wherein the judgment section judges user's disappointment with the use of a template.

3. The service providing system of claim 1, further comprising:
   a learning section that learns a relationship between the user's request and the response content with use of the judgment result by the judgment section.

4. The service providing system of claim 1,
   wherein help indication is provided as service.

5. The service providing system of claim 1,
   wherein service is provided as an agent.

6. The service providing system of claim 1, wherein service is provided through natural conversation.

7. A disappointment judging system, comprising:

an input section that receives user's request;

a response determination section that determines a response content in response to the user's request received by the input section;

an output section that outputs the response content determined by the response content determination section;

a biological signal detection section that measures user's event-related potential from a timing, as a starting point, when the output section outputs the response content; and a judgment section that judges user's disappointment using a part around approximately 600 ms after the starting point of the event-related potential measured by the biological signal detection section.

8. A disappointment judging method for judging user's disappointment in a service providing system, comprising:

an inputting step of receiving user's request;

a response content determining step of determining a response content in response to the request received in the inputting step;

an outputting step of outputting the response content determined in the response content determining step;

a biological signal detecting step of measuring user's event-related potential from a timing, as a starting point, when the response content is output in the outputting step; and a judging step of judging user's disappointment using a part around approximately 600 ms after the starting point of the event-related potential measured in the biological signal detecting step.

* * * * *

UNITED STATES PATENT AND TRADEMARK OFFICE
CERTIFICATE OF CORRECTION

PATENT NO. : 7,536,270 B2  Page 1 of 1
APPLICATION NO. : 11/319082
DATED : May 19, 2009
INVENTOR(S) : Koji Morikawa et al.

It is certified that error appears in the above-identified patent and that said Letters Patent is hereby corrected as shown below:

On page 2 of the title page, the author of the third reference under "Other Publications" listed as "HIroshi Nittono" should read -- Hiroshi Nittono --

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,536,270 B2 | Page 1 of 1 |
| APPLICATION NO. | : 11/319082 | |
| DATED | : May 19, 2009 | |
| INVENTOR(S) | : Morikawa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 613 days.

Signed and Sealed this
Eighth Day of March, 2011

David J. Kappos
*Director of the United States Patent and Trademark Office*